United States Patent [19]

Siedle et al.

[11] Patent Number: 4,625,069
[45] Date of Patent: Nov. 25, 1986

[54] FLUOROCHEMICAL RHODIUM COMPOUNDS

[75] Inventors: Allen R. Siedle, Lake Elmo; Richard D. Howells, St. Paul, both of Minn.

[73] Assignee: Minnesota Mining and Manufacturing, St. Paul, Minn.

[21] Appl. No.: 769,590

[22] Filed: Aug. 26, 1985

Related U.S. Application Data

[62] Division of Ser. No. 541,129, Oct. 12, 1983, Pat. No. 4,556,720.

[51] Int. Cl.$^4$ ............................................. C07C 45/50
[52] U.S. Cl. .................................................... 568/454; 585/253; 585/377; 585/407
[58] Field of Search .................... 568/454, 909; 260/429 R, ; 585/253, 377, 407

[56] References Cited

U.S. PATENT DOCUMENTS

| | | | |
|---|---|---|---|
| 3,794,671 | 2/1974 | Wilkenson | 260/429 R |
| 4,302,401 | 11/1981 | Oswald | 260/429 R |
| 4,376,870 | 3/1983 | Christopfel et al. | 260/429 R |
| 4,415,500 | 11/1983 | Manassen et al. | 260/429 R |
| 4,451,673 | 5/1984 | Oswald et al. | 568/454 |

FOREIGN PATENT DOCUMENTS 871144  6/1961  United Kingdom ............ 260/429 R

OTHER PUBLICATIONS

Blum et al., "J. Org. Chem." vol. 35(6), pp. 1895–1899 (1970).
Porta et al., "J. Organometallic Chemistry" vol. 194, pp. 211–220 (1980).
Parshall "Homogenous Catalysis" Wiley & Sons, NY, NY (1980), pp. 31–169.
Yared et al., "J. Amer. Chem. Soc." vol. 99, p. 7076 (1977).
A. Yamamoto, S. Kitazuma and S. Ikeda; J. Am. Chem. Soc. 90, 1098 (1968).
K. C. Dewhirst, et al.; Inorg. Chem. 7, 546 (1968).
R. R. Schrock et al., J. Am. Chem. Soc., 93, 2397 (1971).
Chemical Abstracts 72 12853e (1970).
Chemical Abstracts 93 185345c (1980).

*Primary Examiner*—Werren B. Lone
*Attorney, Agent, or Firm*—Donald M. Sell; James A. Smith; Lorraine R. Sherman

[57] ABSTRACT

Coordination compounds of rhodium are solid salts having donor ligands of [(aryl)$_3$P]$_3$Rh$^+$ and a non-coordinated counterion derived from a fluorochemical acid, the salts having the formula:

[(aryl)$_3$P]$_3$Rh$^+$ (counterion)$^-$.

The salts are prepared by reacting [(aryl)$_3$P]$_4$RhH, which is and uncharged rhodium hydride, with a fluorochemical acid selected form acids having the formulae:

HC(R)(SO$_2$R$_f$)$_2$, R$_f$SO$_3$H, and HN(SO$_2$R$_f$)$_2$ wherein R$_f$ and R$_f'$ are perfluoroalkyl groups and R is lower alkyl substituted or unsubstituted phenyl, hydrogen, Cl, SO$_2$R$_f$ or R$_f$. Carbonylation of the [(aryl)$_3$P]$_3$Rh$^+$ (counterion)$^-$ compounds of this invention, e.g., by contacting the salts of the invention with carbon monoxide gas, produces salts having the formula:

[(aryl)$_3$P]$_3$Rh(CO)$_n$$^+$(counterion)$^-$, wherein n is 1 or 2, and (counterion)$^-$ is as defined above. These carbonylated derivatives as well as the above-described precursor salts are useful as catalysts in organic transformation reactions, such as isomerization, cyclization and hydroformylation reactions.

12 Claims, No Drawings

FLUOROCHEMICAL RHODIUM COMPOUNDS

This is a division of application Ser. No. 541,129, filed Oct. 12, 1983, now U.S. Pat. No. 4,556,720.

FIELD OF THE INVENTION

This invention relates to coordination compounds of rhodium(I), carbonylated derivatives thereof, and to methods of preparing them. In another aspect, it relates to compositions of matter containing the rhodium(I) coordination compounds of their carbonylated derivatives as catalysts.

BACKGROUND ART

Organometallic compounds containing rhodium have been widely used as intermediates and catalysts. An outstanding example is "Wilkinson's Catalyst", [(C$_6$H$_5$)$_3$P]$_3$RhCl, wherein (C$_6$H$_5$)$_3$P is triphenylphosphine [see G. W. Parshall, "Homogenous Catalysis", John Wiley & Sons, New York, N.Y., 8 (1980)]. It is perhaps the most versatile organic rhodium catalyst known. It has a square planar structure with the three (C$_6$H$_5$)$_3$P ligands and one chloride ligand in an array about a central rhodium atom:

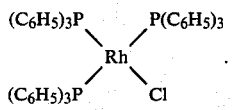

It is known in the art that "Wilkinson's Catalyst" undergoes equilibrium dissociation to produce [(C$_6$H$_5$)$_3$P]$_2$RhCl, a highly reactive, three-coordinate, 14-electron intermediate, and one uncoordinated triphenylphosphine liquid. The dissociation reaction is as follows:

$$[(C_6H_5)_3P]_3RhCl \rightleftharpoons (C_6H_5)_3P + [(C_6H_5)_3P]_2RhCl$$

The structural features of the intermediates contribute to high chemical reactivity in two ways: (1) Rh(I) normally is four coordinate and thus the "vacant" site in a three coordinate compound provides a binding site for a substrate molecule which will subsequently undergo a catalytic transformation; and (2) Rh(I) normally has 16 electrons in its outer shell, consequently, species with a 14 electron configuration will react rapidly with electron donor compounds such as alkenes, alkynes, carbon monoxide, nitric oxide and other compounds that will provide the needed extra electrons.

The prior art teaches the preparation and use of tris(triarylphosphine)rhodium(I) complexes having an anion coordinated to the central rhodium atom. A. Yamamoto, S. Kitazuma and S. Ikeda in J. Am. Chem. Soc. 90, 1089 (1968) disclose [(C$_6$H$_5$)$_3$P]$_4$RhH and report that 0.4 mole of hydrogen per mole of Rh is liberated on acidolysis; the acid used is not disclosed and the product(s) of the reaction other than hydrogen are not isolated or characterized. Furthermore, no uses for the products are taught. K. C. Dewhirst et al. in Inorg. Chem. 7, 546 (1968), employ phenol as a proton source and note that its reaction with [(C$_6$H$_5$)$_3$P]$_n$RhH, wherein n is 3 or 4, produces [(C$_6$H$_5$)$_3$P]$_{n-1}$RhOC$_6$H$_5$. Again, the conjugate base of the acid remains bonded to the metal.

Yared et al., J. Am. Chem. Soc. 99, 7076 (1977) disclose certain rhodium perchlorate salts, i.e., [(C$_6$H$_5$)$_3$P]$_3$Rh$^+$ClO$_4^-$ and [(C$_6$H$_5$)$_3$P]$_3$Rh(CO)$_2^+$ ClO$_4^-$. Perchlorate salts of cations containing organic groups are generally recognized to be explosive.

U.S. Pat. No. 3,794,671 discloses a method of making Rh(I) compounds of the type [(C$_6$H$_5$)$_3$P]$_3$Rh$^+$(anion)$^-$, where the anion is fluoroborate (BF$_4^-$), acetate, trifluoromethanesulfonate (CF$_3$SO$_3^-$), trifluoroacetate, or benzoate. These compounds are useful as catalysts in organic reactions such as hydrogenation, isomerization, and hydroformylation of olefins. In col. 3, lines 69–71, the patentee suggests that an ionic species is not present in [(C$_6$H$_5$)$_3$P]$_3$Rh$^+$BF$_4^-$ and that coordination to the BF$_4^-$ ion exists. U.S. Pat. No. 3,794,671 also discloses certain rhodium carboxylates having the formula [(C$_6$H$_5$)$_3$P]$_3$Rh(OCOR), wherein R is substituted or unsubstituted alkyl or aryl, and [(C$_6$H$_5$)$_3$P]$_3$Rh(CO)BF$_4$, the latter having been prepared by reaction of [(C$_6$H$_5$)$_3$]P$_3$RhBF$_4$ and CO.

R. R. Schrock et al., J. Am. Chem. Soc. 93, 2397 (1971) disclose various rhodium coordination compounds including [(C$_6$H$_5$)$_3$P]$_3$Rh(CO)$^+$ClO$_4^-$ and [(C$_6$H$_5$)$_3$P]$_3$Rh(CO)$_2$$^+$B(C$_6$H$_5$)$_4^-$. In this publication, the routes (solution phase) to cationic rhodium carbonyl compounds employ as starting materials cationic olefin complexes of rhodium.

SUMMARY OF THE INVENTION

Briefly, in one aspect, the present invention provides coordination compounds of rhodium that are salts containing (1) a donor ligand and (2) a non-coordinated counterion derived from a fluorochemical acid. The salts are normally solid, three-coordinate Rh(I) compounds that are cationic triarylphosphine coordination compounds of Rh(I) and a non-coordinating counteranion derived from a fluorochemical acid, the salts having the formula:

$$[(aryl)_3P]_3Rh^+(counterion)^-.$$

The salts can be prepared by reacting [(aryl)$_3$P]$_4$RhH, which is an uncharged rhodium hydride, with a fluorochemical acid selected from acids having the formulae:

$$HC(R)(SO_2R_f)_2, \; R_fSO_3H, \; \text{and} \; HN(SO_2R_f)_2$$

wherein $R_f$ is a perfluoroalkyl group having 1 to 20 carbon atoms, $R_f'$ is identical to $R_f$ except that it contains at least 4 carbon atoms, i.e., it can have 4 to 20 carbon atoms, and R is a lower alkyl group having 1 to 4 carbon atoms, unsubstituted phenyl or phenyl substituted by straight chain or branched alkyl having 1 to 20 carbon atoms, Cl, SO$_2$R$_f$, R$_f$, or hydrogen, wherein R$_f$ is as just defined.

The coordination compounds of this invention are readily soluble in nonaqueous common organic solvents and provide a stable and convenient source of Rh(I) in a highly reactive form, this valency state of the metal having particular importance in catalytic transformations of organic compounds.

Carbonylation of the [(aryl)$_3$P]$_3$Rh$^+$(counterion)$^-$ compounds of this invention, e.g., by contacting the dry salts of the invention with carbon monoxide gas, produces salts having the formula:

$$[(aryl)_3P]_3Rh(CO)_n^+(counterion)^-,$$

wherein n is 1 or 2 and (counterion)$^-$ is as defined above. These carbonylated derivatives as well as the above-described precursor salts are useful as catalysts in organic transformation reactions.

Rhodium compounds of the present invention differ from prior art rhodium compounds in that the counterion is not coordinated to the central rhodium atom but exists as a separate, fluorine-containing ionic species. Electrical conductance measurements confirm the ionic nature of the present invention compounds. U.S. Pat. No. 3,794,671, col. 3, lines 67–72, discloses that conductivity measurements on tris(triphenylphosphine)rhodium(I) fluoroborate in nitromethane solution were performed and that its conductivity was considerably less than that required for a 1:1 electrolyte. In contrast to those results, compounds of the present invention are 1:1 electrolytes as supported by conductivity measurements in acetonitrile solution, a solvent whose dielectric constant is close to that of nitromethane (compounds of this invention are not stable in nitromethane). In the present invention, only a certain class of anions can be used. Furthermore, compounds of the invention are soluble in nonaqueous common organic solvents such as benzene, toluene, dichloromethane, chloroform, and acetonitrile. They can be easily and safely prepared from less toxic and nonexplosive starting materials than can prior art compounds and the products and nonexplosive and readily handled. They are useful as catalysts for the transformation of organic compounds, such as isomerization, cyclization, and hydroformylation reactions.

Further, prior art carbon monoxide-containing analogs of rhodium(I) compounds have not been derived from fluorochemical acids as described in the present invention and all prior art carbonylated rhodium(I) compounds require use of an organic solvent such as methanol or benzene in their preparation. The advantages in terms of economy and convenience of solventless methods of manufacture are, of course, well known in the art.

As used in the present application:

"counterion" means the conjugate base of an above-described fluorochemical acid.

"carbonylation" means reaction between carbon monoxide and an inorganic or organometallic compound in which carbon monoxide is incorporated into a molecule;

"fluorochemical acid" means a perfluorosulfonic acid, a bis(perfluoroalkylsulfonyl)alkane or a bis(perfluoroalkylsulfonyl)amine, or derivatives thereof wherein the perfluoroalkyl radical has 1 to 20 carbon atoms and the alkyl group of the alkane acid portion of the molecule has 1 to 4 carbon atoms;

"hydroformylation" means the addition of two hydrogen atoms and carbon monoxide to an olefin to produce an aldehyde, e.g., conversion of 1-hexane to heptaldehyde; and "catenary" means in the main chain or backbone.

DETAILED DESCRIPTION

Coordination compounds of rhodium(I) having the formula

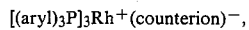

[(aryl)$_3$P]$_3$Rh$^+$(counterion)$^-$, and carbonylated derivatives thereof having the formula

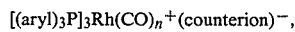

[(aryl)$_3$P]$_3$Rh(CO)$_n$$^+$(counterion)$^-$, and a method therefor, are provided by the present invention wherein aryl is unsubstituted phenyl, phenyl substituted by 1 to 3 methyl groups, e.g., aryl can be tolyl or xylyl, but preferably it is phenyl, or for one aryl group it can be polystyryl, n is the integer 1 or 2, and (counterion)$^-$ is the conjugate base of certain fluorochemical acids, i.e., it is derived from certain fluorochemical acids by loss of a porton.

Suitable fluorochemical acids for use in the present invention include H$_2$C(SO$_2$R$_f$)$_2$ and HC(R)(SO$_2$R$_f$)$_2$, such as H$_2$C(SO$_2$CF$_3$)$_2$, H$_2$C(SO$_2$C$_4$F$_9$)$_2$, H$_2$C(SO$_2$C$_8$F$_{17}$)$_2$, HC(C$_6$H$_5$)(SO$_2$CF$_3$)$_2$, C$_8$F$_{17}$SO$_3$H, and NH(SO$_2$R$_f$)$_2$ such as NH(SO$_2$CF$_3$)$_2$, wherein R$_f$ is a fluoroaliphatic group having 1 to 20 carbon atoms, and wherein R is a lower alkyl group having 1 to 4 carbon atoms, phenyl, Cl, SO$_2$R$_f$ and R$_f$, wherein R$_f$ is as just defined.

The fluoroaliphatic radical, R$_f$, is a fluorinated, stable, inert, non-polar, preferably saturated, monovalent moiety which is both oleophobic and hydrophobic. It can be straight chain, branched chain, and, if sufficiently large, cyclic, or combinations thereof, such as fluoroalkylcycloaliphatic radicals. The skeletal chain can include catenary oxygen, hexavalent sulfur, and/or trivalent nitrogen hetero atoms bonded only to carbon atoms, such hetero atoms providing stable linkages between fluorocarbon portions of R$_f$ and not interfering with the inert character of the R$_f$ radical. While R$_f$ can have a large number of carbon atoms, compounds where R$_f$ is not more than 20 carbon atoms will be adequate and preferred since large radicals usually represent a less efficient utilization of fluorine than is possible with smaller R$_f$ radicals. The large radicals also are generally less soluble in organic solvents. Generally, R$_f$ will have 1 to 20 carbon atoms, preferably 1 to about 8, and will contain 40 to 83 weight percent, preferably 50 to 83 weight percent, fluorine. The terminal portion of the R$_f$ groups having 3 or more carbon atoms have at least three fully fluorinated carbon atoms, e.g., CF$_3$CF$_2$CF$_2$—, and the preferred compounds are those in which the R$_f$ group is fully or substantially completely fluorinated, as in the case where R$_f$ is perfluoroalkyl, C$_n$F$_{2n+1}$. Commercially available R$_f$-containing products generally are mixtures of such compounds with the number of carbon atoms in the R$_f$ moieties of the compounds varying, and in the formulas herein for such compounds the recited number of carbon atoms in the fluoroaliphatic radical (unless indicated otherwise) is an average of the fluoroaliphatic carbon atoms in the mixture. In this application the given number of carbon atoms in the R$_f$ moieties of the fluorochemical acids, their conjugate bases, and other fluorochemicals should likewise be understood to be an average number unless indicated otherwise.

The preferred counterions of the present invention compounds are HC(SO$_2$R$_f$)$_2$$^-$, C$_8$F$_{17}$SO$_3$$^-$, C$_8$F$_{15}$SO$_3$$^-$, and N(SO$_2$R$_f$)$_2$$^-$, where R$_f$ is C$_n$F$_{2n+1}$ and n is 1, 4 or 8.

In the process of the invention, tetrakis(triarylphosphine)rhodium(I)hydride, [(aryl)$_3$P]$_4$RhH, which in the preferred embodiment is tetrakis(triphenylphosphine)rhodium(I)hydride, [(C$_6$H$_5$)$_3$P]$_4$RhH, reacts in a 1:1 molar ratio with the above-mentioned fluorochemical acids in organic solvents to form hydrogen, triphenylphosphine and [(aryl)$_3$P]$_3$Rh$^+$(counterion), according to the reaction:

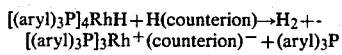
[(aryl)$_3$P]$_4$RhH + H(counterion)$^-$ → H$_2$ + [(aryl)$_3$P]$_3$Rh$^+$(counterion)$^-$ + (aryl)$_3$P As a result of this reaction, the coordination number of the Rh atom decreases from 5 to 3.

Organic solvents useful for the reaction include ethers having up to 8 carbon atoms, such as diethyl ether and tetrahydrofuran; chlorinated lower straight or branched-chain aliphatic (C$_1$ to C$_4$) hydrocarbons such as dichloromethane; and unsubstituted and alkyl-substituted aromatic hydrocarbons having up to 9 carbon atoms, such as benzene and toluene. Toluene is the preferred solvent when the R$_f$ group in the fluorochemical acid is CF$_3$ since the desired rhodium compounds precipitate from the reaction mixture and can be isolated by filtration or centrifugation; furthermore, the triphenylphosphine by-product remains in solution. The rhodium compounds of this invention in which R$_f$ is C$_4$F$_9$ or C$_8$F$_{17}$ (straight or branched chain, cyclic, or mixtures thereof, but preferably straight-chain) are, surprisingly, soluble in aromatic hydrocarbons such as benzene, toluene, or xylene, and 0.2 molar solutions of [(C$_6$H$_5$)$_3$P]$_3$Rh$^+$HC(SO$_2$C$_8$F$_{17}$)$_2$$^-$ in toluene can readily be prepared. Use, as described in the present invention, of R$_f$SO$_3$H as opposed to use of CF$_3$SO$_3$H as disclosed in U.S. Pat. No. 3,794,671 provides the advantage that the resulting R$_f$SO$_3$$^-$ salts of the present invention are ready soluble in aromatic hydrocarbons. Thus [(C$_6$H$_5$)$_3$P]$_3$Rh$^+$C$_8$F$_{17}$SO$_3$$^-$ dissolves readily in, for example, benzene, toluene, and xylene. Further, the R$_f$SO$_3$H materials are useful relative to CF$_3$SO$_3$H, in that they are more easily and safely handled. Trifluoromethanesulfonic acid is a fuming, corrosive liquid which must be protected from air in order that it not absorb moisture. The R$_f$SO$_3$H acids, as exemplified by C$_8$F$_{17}$SO$_3$H, are solids which have little or no tendency to absorb moisture.

In catalysis reactions, the fact that the compounds of the invention containing perfluoroalkyl groups are soluble in a variety of organic solvents such as benzene, toluene, dichloromethane, chloroform, and acetonitrile permits their use as catalysts in homogeneous systems.

Although [(C$_6$H$_5$)$_3$P]$_3$Rh$^+$HC(SO$_2$CF$_3$)$_2$$^-$, is itself quite soluble in organic solvents, it may be used to attach triphenylphosphine rhodium-containing moieties to polymeric substrates, thereby providing Rh(I) in an insoluble form which may be readily retrieved from reaction mixtures. Uses and advantages of resin-bound rhodium containing reagents are well known in the art having been pointed out, for example, by Collman et al. [J. P. Collman, L. S. Hegedus, M. P. Cooke, J. R. Norton, G. Dolcetti and D. N. Marquardt, J. Am. Chem. Soc., 94, 1789 (1972)]. Thus, when resin-substituted triphenylphosphine was contacted with a dichloromethane solution of [(C$_6$H$_5$)$_3$P]$_3$Rh$^+$HC(SO$_2$CF$_3$)$_2$$^-$ (less than or equal to 1 mole, and preferably 0.1 to 1 mole of Rh compound per mole of P in the polymer), the surface of the pale orange polymer turned red, indicating that [(C$_6$H$_5$)$_3$P]$_2$Rh$^+$ units had become bonded to the phosphine donor sites on the polymer.

As described in the examples below, [(C$_6$H$_5$)$_3$P]$_3$Rh$^+$HC(SO$_2$CF$_3$)$_2$$^-$, and other compounds within the scope of the invention containing non-coordinating fluorochemical anions, are useful in olefin isomerization such as conversion of 1-pentene to 2-pentene, olefin hydroformylation such as conversion of 1-hexene to heptaldehyde, and in a cyclotrimerization reaction of alkynes such as conversion of hexafluorobutyne to hexakis(trifluoromethylene)benzene. These reactions are discussed in the reference, G. W. Parshall, "Homogeneous Catalysis", John Wiley and Sons, NY, pp. 32, 86, 87, 163, 164 (1980) which is incorporated herein by reference.

Carbonylation of the [(aryl)$_3$P]$_3$Rh$^+$(counterion)$^-$ compounds of this invention, by contacting the solid compounds with carbon monoxide gas, produces [(aryl)$_3$P]$_3$Rh(CO)$_2$$^+$(counterion)$^-$. For example, when red [(C$_6$H$_5$)$_3$P]$_3$Rh$^+$HC(SO$_2$CF$_3$)$_2$$^-$ is subjected to one or more atmospheres pressure of carbon monoxide, the gas is rapidly absorbed and yellow [(C$_6$H$_5$)$_3$P]$_3$Rh(CO)$_2$$^+$HC(SO$_2$CF$_3$)$_2$$^-$ is produced, as confirmed by spectroscopic analysis. When lower pressures of carbon monoxide are used, [(C$_6$H$_5$)$_3$P]$_3$Rh(CO)$^+$(counterion)$^-$ is concomitantly produced. This mixture may be converted to pure [(C$_6$H$_5$)$_3$P]$_3$Rh(CO)$_2$$^+$(counterion)$^-$ by treatment with one or more atmospheres of CO gas. Alternatively, the dicarbonyl compound may be converted to pure [(C$_6$H$_5$)$_3$P]$_3$Rh(CO)$^+$(counterion)$^-$ by recrystallization as described below. When [(aryl)$_3$P]$_3$Rh(CO)$_2$$^+$(counterion)$^-$ salts produced by this method dissolved in organic solvents, such as chlorinated aliphatic hydrocarbons of 1 to 4 carbon atoms, such as dichloromethane, ethers of 2 to 8 carbon atoms, such as tetrahydrofuran or 1,2-dimethoxyethane, or unsubstituted or alkyl-substituted aromatic hydrocarbons of 6 to 9 carbon atoms such as toluene, which solvent is then allowed to evaporate, one equivalent of carbon monoxide is lost and a compound having the formula [(aryl)$_3$P]$_3$Rh(CO)$^+$(counterion)$^-$ is produced. The process can be accelerated by application of a vacuum or by passing an inert gas such as nitrogen or argon through the solution. Alternatively, the process may be carried out in the absence of solvent by application of heat and vacuum. Thus, when a dichloromethane-toluene solution of [(C$_6$H$_5$)$_3$P]$_3$Rh(CO)$_2$$^+$HC(SO$_2$CF$_3$)$_2$$^-$ was concentrated under reduced pressure, [(C$_6$H$_5$)$_3$P]$_3$Rh(CO)$^+$HC(SO$_2$CF$_3$)$_2$$^-$ was formed and was identified by spectroscopic analysis. The original compound, [(C$_6$H$_5$)$_3$P]$_3$Rh(CO)$_2$$^+$HC(SO$_2$CF$_3$)$_2$$^-$, was regenerated by passing a stream of carbon monoxide gas through a dichloromethane solution of [(C$_6$H$_5$)$_3$P]$_3$Rh(CO)$^+$HC(SO$_2$CF$_3$)$_2$$^-$. Thus, either [(aryl)$_3$P]$_3$Rh(CO)$_2$$^+$(counterion)$^-$ or [(aryl)$_3$P]$_3$Rh(CO)$^+$(counterion)$^-$ may be prepared from [(aryl)$_3$P]$_3$Rh$^+$(counterion)$^-$ and carbon monoxide.

An alternative method of preparing [(C$_6$H$_5$)$_3$P]$_3$Rh(CO)$^+$(counterion)$^-$ consists of reacting [(C$_6$H$_5$)$_3$P]$_3$Rh(CO)H in approximately a 1:1 molar ratio with the appropriate fluorochemical acid. For the acid H$_2$C(SO$_2$CF$_3$)$_2$ the reaction is as follows:

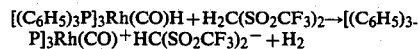
[(C$_6$H$_5$)$_3$P]$_3$Rh(CO)H + H$_2$C(SO$_2$CF$_3$)$_2$ → [(C$_6$H$_5$)$_3$P]$_3$Rh(CO)$^+$HC(SO$_2$CF$_3$)$_2$$^-$ + H$_2$ The reaction is carried out by stirring a mixture of the two reactants under nitrogen with a solvent such as benzene, toluene or xylene; toluene is the preferred solvent. Use of aromatic hydrocarbon solvents is convenient since the starting materials are soluble in them whereas the product salt is not. The product separates as a yellow, air- and moisture-stable solid which is isolated by filtration. Recrystallization of [(C$_6$H$_5$)$_3$P]Rh(CO)$^+$HC(SO$_2$CF$_3$)$_2$$^-$ from acetone-toluene is a useful means of removing any acetone-insoluble impurity sometimes found in $[(C_6H_5)_3P]_3Rh(CO)H$. This procedure yields a solvate containing about 0.75 mole of toluene per mole of rhodium. While this material is sufficiently pure for synthetic purposes, a solvent-free salt may be obtained by recrystallization from ethanol. Other fluorochemical acids that can be used in this method include $C_6H_5CH(SO_2CF_3)_2$ and $HN(SO_2CF_3)_2$ from which are obtained, respectively, the $C_6H_5C(SO_2CF_3)_2^-$ and $N(SO_2CF_3)_2^-$ salts of $[(C_6H_5)_3P]_3Rh(CO)^+$.

Objects and advantages of this invention are further illustrated by the following examples, but the particular materials and amounts thereof recited in these examples, as well as other conditions and details, should not be construed to unduly limit this invention.

EXAMPLE 1

Synthesis of $[(C_6H_5)_3P]_3Rh^+HC(SO_2CF_3)_2^-$

Toluene (purified by distillation from sodium-benzophenone), 18 ml, was added to a nitrogen-filled flask containing 0.57 g (0.5 mmole) $[(C_6H_5)_3P]_4RhH$ [prepared as in Ahmed et al., Inorg. Syn. 15, 59 (1974)] and 0.14 g $H_2C(SO_2CF_3)_2$ [prepared by the method described in R. J. Koshar et al., J. Org. Chem. 38, 3358 (1973)]. This reaction mixture was stirred for 16 hours at room temperature. Filtration under dry nitrogen provided 0.5 g (84 percent) of the product as a red powder. Chemical and spectroscopic analysis confirmed the product to be $[(C_6H_5)_3P]_3Rh^+HC(SO_2CF_3)_2^-$.

A $1.3 \times 10^{-3}$ molar solution in acetonitrile of the compound prepared in EXAMPLE 1 had a molar conductance of 129 ohm$^{-1}$ cm$^2$ mole$^{-1}$ which is in the expected range for 1:1 electrolytes, the molar conductance of which are reported to range from 120–160 ohm$^{-1}$ cm$^2$ mole$^{-1}$ according to W. J. Geary, Coord. Chem. Rev. 7, 81, 110, (1971).

EXAMPLE 2

Synthesis of $[(C_6H_5)_3P]_3Rh^+C_6H_5C(SO_2CF_3)_2^-$

This salt was prepared using the method of EXAMPLE 1 except that $C_6H_5CH(SO_2CF_3)_2$ (prepared as described by R. J. Koshar et al., supra) was used in place of $H_2C(SO_2CF_3)_2$. Chemical and spectroscopic analysis confirmed the identity of the product.

EXAMPLE 3

Red $[(C_6H_5)_3P]_3Rh^+N(SO_2CF_3)_2^-$ was prepared by the method of EXAMPLE 1 using $HN(SO_2CF_3)_2$ prepared as described in German Offenlegungschrift No. 2,239,817 (1974) instead of $H_2C(SO_2CF_3)_2$. Spectroscopic analysis confirmed the identity of the product.

EXAMPLE 4

A mixture of 1.0 g $[(C_6H_5)_3P]_4RhH$, 0.85 g $H_2C(SO_2C_8F_{17})_2$ (prepared as described in R. J. Koshar et al., supra) and 10 ml of dichloromethane was stirred under a nitrogen atmosphere for 30 min. Hexane, 5 ml, was added and the dichloromethane was gradually evaporated under reduced pressure. When a red oil separated and the supernatent liquid was light pink, the oil was decanted and dried under high vacuum. The resulting red powder weighed 1.2 g and was identified by spectroscopic analysis to be $[(C_6H_5)_3P]_3Rh^+HC(SO_2C_8F_{17})_2^-$.

EXAMPLE 5

$[(C_6H_5)_3P]_3Rh^+HC(SO_2C_4F_9)_2^-$ was prepared by the method of EXAMPLE 4 using $H_2C(SO_2C_4F_9)_2$ prepared as in R. J. Koshar et al., supra) instead of $H_2C(SO_2C_8F_{17})_2$. Product identity was confirmed by spectroscopic analysis.

EXAMPLE 6

$[(p\text{-Tolyl})_3P]_3Rh^+HC(SO_2C_4F_9)_2^-$ was prepared by the method of EXAMPLE 5 using $[(p\text{-tolyl})_3P]_4RhH$ [prepared by the method of Ahmed et al. except that $(p\text{-tolyl})_3P$ was substituted for $(C_6H_5)_3P$] in place of $[(C_6H_5)_3P]_4RhH$. The identity of the resulting red product was confirmed by spectroscopic analysis.

EXAMPLE 7

Synthesis of $[(C_6H_5)_3P]_3Rh^+C_8F_{17}SO_3^-$

Oxygen-free dichlormethane, 6 ml, was added to a mixture of 0.38 gm $[(C_6H_5)_3P]_4RhH$ and 0.17 gm $C_8F_{17}SO_3H$. The reaction mixture was stirred under nitrogen for 30 min. Solvent was removed from the resulting clear, red solution under reduced pressure. In a nitrogen atmosphere, the residue was extracted with four 5 ml portions of warm hexane. The remaining solids were then vacuum dried to give 0.41 gm of red, powdery $[(C_6H_5)_3P]_3Rh^+C_8F_{17}SO_3^-$ which was identified by spectroscopic analyses. This compound dissolved in toluene to give a red solution.

EXAMPLE 8

Carbonylation of solid $[(C_6H_5)_3P]_3Rh^+HC(SO_2CF_3)_2^-$

A slurry of 8.95 g $[(C_6H_5)_3P]_4RhH$ (prepared as in EXAMPLE 1) in 75 ml oxygen-free toluene was stirred for 24 hr. with 2.3 g of $H_2C(SO_2CF_3)_2$. The red, powdery $[(C_6H_5)_3P]_3Rh^+HC(SO_2CF_3)_2^-$ was recovered by filtration and dried by application of a vacuum. It was then transferred to a nitrogen-filled flask which was attached to a vacuum line. The flask was evacuated and pressurized to 800 mm with carbon monoxide. A rapid pressure drop due to consumption of carbon monoxide and an exotherm were noted. The carbon monoxide pressure was kept at 800 mm and after 30 min the yellow solid product $[(C_6H_5)_3P]_3Rh(CO)_2^+HC(SO_2CF_3)_2^-$, was removed. The weight of product was 8.8 g, representing a 95 percent yield based on $[(C_6H_5)_3P]_4RhH$. Chemical and spectroscopic analyses confirmed the identity of the product.

EXAMPLE 9

Dry, oxygen-free toluene, 20 ml, was added under nitrogen to 2.68 g $[(C_6H_5)_3P]_3Rh(CO)H$, prepared by the method of Ahmed et al., Inorg. Syn., 15, 59 (1974), and 0.64 g $H_2C(SO_2CF_3)$. After stirring overnight, the reaction mixture was filtered to provide, after vacuum drying, 2.69 g of the precipitated product, $[(C_6H_5)_3P]_3Rh(CO)^+HC(SO_2CF_3)_2^-$. An analytical sample was prepared by recrystallization from ethanol. Chemical and spectroscopic analyses confirmed the identity of the product.

EXAMPLE 10

$[(C_6H_5)_3P]_3Rh(CO)H$, 0.84 g, and 0.27 g $HN(SO_2CF_3)_2$ were allowed to react in 10 ml toluene as described in EXAMPLE 1. The orange solid product was recrystallized from acetone-toluene to yield 0.93 g of $[(C_6H_5)_3P]_3Rh(CO)^+N(SO_2CF_3)_2^-$ which was essentially free of toluene by $^1H$ NMR analysis. Chemical and spectroscopic analyses confirmed the identity of the product.

EXAMPLE 11

$[(C_6H_5)_3P]_3Rh(CO)H$, 0.84 g, and 0.32 g of $C_6H_5CH(SO_2CF_3)_2$ were allowed to react in 12 ml toluene as described in EXAMPLE 1. The crude yellow solid was recrystallized from acetone-toluene to give 0.86 g of pure $[(C_6H_5)_3P]_3Rh(CO)^+C_6H_5C(SO_2CF_3)^-$ essentially free of toluene by $^1H$ NMR analysis. Chemical analysis confirmed the identity of the product.

EXAMPLE 12

Cyclotrimerization of hexafluorobutyne

A 0.25 g sample of $[(C_6H_5)_3P]_3Rh^+HC(SO_2CF_3)_2^-$, prepared according to the method of EXAMPLE 1, was loaded into a flask in a nitrogen atmosphere. Dichloromethane, 7 ml, and hexafluoro-2-butyne, 0.5 ml, were added by vacuum transfer. The tube was heated at 80° C. overnight, then cooled to room temperature. Hexakis(trifluoromethyl)benzene, 0.1 g, separated as a yellow powder and was identified by spectroscopic analysis.

EXAMPLE 13

Isomerization of 1-pentene

A 0.05 g sample of $[(C_6H_5)_3P]_3Rh^+HC(SO_2CF_3)_2^-$, prepared according the method of EXAMPLE 1, was placed in an NMR tube. 1-Pentene, 0.2 ml, and $CD_2Cl_2$, 0.5 ml, were added by vacuum transfer. The contents of the tube were kept at room temperature for 4 weeks. Analysis by $^{13}C$ NMR spectroscopy revealed that the sample then contained trans-2-pentene and cis-2-pentene in a 9:1 ratio; no 1-pentene remained.

EXAMPLE 14

Hydroformylation of 1-hexene

Toluene, 13.8 ml, 1-hexene, 1.2 ml, and 0.1 g $[(C_6H_5)_3P]_3Rh(CO)_2^+HC(SO_2CF_3)_2^-$, prepared according to the method of EXAMPLE 7, were placed in an autoclave. The vessel was evacuated and then pressurized to 69 kg/cm$^2$ (1000 psig) with a 1:1 mixture of hydrogen and carbon monoxide. After heating overnight at 100° C., the autoclave was cooled to room temperature, vented and the product removed. Analysis by gas chromatography showed that heptanal, n-hexane and 1-hexene were present in a ratio of 634:8:1.

EXAMPLE 15

Insolubilization of $[(C_6H_5)_3P]_3Rh^+HC(SO_2CF_3)_2^-$

A 0.33 g sample of triphenylphosphine-substituted polystyrene (Aldrich Chemical Co.) was stirred under nitrogen with a solution of 0.55 g $[(C_6H_5)_3P]_3Rh^+HC(SO_2CF_3)_2^-$ in 6 ml of dichloromethane. After 2.5 hr. the red colored product was isolated by filtration, washed with fresh solvent, vacuum dried and stored under nitrogen. Elemental analysis revealed that the polymer now contained 5.3 percent rhodium by weight. The infrared spectrum of this material exhibited characteristic bands due to the $HC(SO_2CF_3)_2^-$ anion.

Various modifications and alterations of this invention will become apparent to those skilled in the art without departing from the scope and spirit of this invention, and it should be understood that this invention is not to be unduly limited to the illustrative embodiments set forth therein.

We claim:

1. In a process for olefin isomerization comprising the steps of:

reacting an olefin compound having at least one carbon-to-carbon double bound in the presence of a catalytically effective amount of a coordination compound of rhodium, optionally in the presence of heat, and recovering the resulting isomerized olefin product, the improvement comprising using as said catalyst a rhodium coordination compound having the formula:

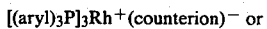

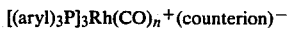

wherein aryl is phenyl, phenyl substituted by 1 to 3 methyl groups, or for one aryl group, polystyryl, n is the integer 1 or 2, (counterion)$^-$ is the conjugate base of acids selected from $HC(R)(SO_2R_f)_2$, $R_f'SO_3H$, and $HN(SO_2R_f)_2$ wherein $R_f$ is a perfluoroalkyl group having 1 to 20 carbon atoms, $R_f'$ is a perfluoroalkyl group having 4 to 20 carbon atoms, and R is lower alkyl, phenyl, Cl, H, $SO_2R_f$, or $R_f$.

2. The process according to claim 1 wherein the (counterion)$^-$ of said coordination compound is $HC(SO_2CF_3)_2^-$, $HC(SO_2C_4F_9)_2^-$, $HC(SO_2C_8F_{17})_2^-$, $C_6H_5C(SO_2CF_3)_2^-$, $N(SO_2CF_3)_2^-$, $C_8F_{17}SO_3^-$, or $C_8F_{15}SO_3^-$.

3. The process according to claim 1 wherein R in the (counterion-) of said coordination compound is lower alkyl, phenyl, or hydrogen.

4. The process according to claim 1 wherein said coordination compound is selected from the class consisting of

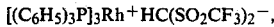

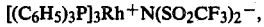

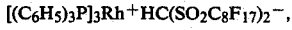

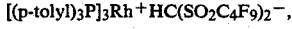

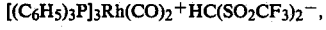

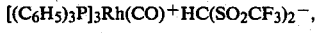

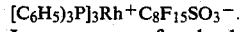

5. In a process for hydroformylation of an olefin compound comprising the steps of:

reacting an olefin having at least one carbon-to-carbon double bond and a mixture of hydrogen and carbon monoxide, in the presence of a catalytically effective amount of a coordination compound of rhodium, heating the resulting mixture, and recovering the resulting aldehyde product, the improvement comprising using as said catalyst a rhodium coordination compound having the formula:

[(aryl)$_3$P]$_3$Rh$^+$(counterion)$^-$ or

[(aryl)$_3$P]$_3$Rh(CO)$_n$$^+$(counterion)$^-$ wherein aryl is phenyl, phenyl substituted by 1 to 3 methyl groups, or for one aryl group, polystyryl, n is the integer 1 or 2, (counterion)$^-$ is the conjugate base of acids selected from HC(R)(SO$_2$R$_f'$)$_2$, R$_f$SO$_3$H, and HN(SO$_2$R$_f$)$_2$ wherein R$_f$ is a perfluoroalkyl group having 1 to 20 carbon atoms, R$_f'$ is a perfluoroalkyl group having 4 to 20 carbon atoms, and R is lower alkyl, phenyl, Cl, H, SO$_2$R$_f$, or R$_f$.

6. The process according to claim 5 wherein the (counterion)$^-$ of said coordination compound is HC(SO$_2$CF$_3$)$_2$$^-$, HC(SO$_2$C$_4$F$_9$)$_2$$^-$, HC(SO$_2$C$_8$F$_{17}$)$_2$$^-$, C$_6$H$_5$C(SO$_2$CF$_3$)$_2$$^-$, N(SO$_2$CF$_3$)$_2$$^-$, C$_8$F$_{17}$SO$_3$$^-$, or C$_8$F$_{15}$SO$_3$$^-$.

7. The process according to claim 5 wherein R in the (counterion)$^-$ of said coordination compound is lower alkyl, phenyl, or hydrogen.

8. The process according to claim 5 wherein said coordination compound is selected from the class consisting of:

[(C$_6$H$_5$)$_3$P]$_3$Rh$^+$HC(SO$_2$CF$_3$)$_2$$^-$,

[(C$_6$H$_5$)$_3$P]$_3$Rh$^+$C$_6$H$_5$C(SO$_2$CF$_3$)$_2$$^-$,

[(C$_6$H$_5$)$_3$P]$_3$Rh$^+$N(SO$_2$CF$_3$)$_2$$^-$,

[(C$_6$H$_5$)$_3$P]$_3$Rh$^+$HC(SO$_2$C$_8$F$_{17}$)$_2$$^-$,

[(C$_6$H$_5$)$_3$P]Rh$^+$HC(SO$_2$C$_4$F$_9$)$_2$$^-$,

[(p-tolyl)$_3$P]$_3$Rh$^+$HC(SO$_2$C$_4$F$_9$)$_2$$^-$,

[(C$_6$H$_5$)$_3$P]$_3$Rh(CO)$_2$$^+$HC(SO$_2$CF$_3$)$_2$$^-$,

[(C$_6$H$_5$)$_3$P]$_3$Rh(CO)$^+$HC(SO$_2$CF$_3$)$_2$$^-$,

[(C$_6$H$_5$)$_3$P]$_3$Rh$^+$C$_8$F$_{17}$SO$_3$$^-$, and

[(C$_6$H$_5$)$_3$P]$_3$Rh$^+$C$_8$F$_{15}$SO$_3$$^-$.

9. In a process for the cyclotrimerization of alkynes comprising of steps of:

reacting an alkyne having at least one carbon-to-carbon triple bond, in the presence of a catalytically effective amount of a coordination compound of rhodium, heating the resulting mixture, and recovering the resulting cyclic trimer, the improvement comprising using as said catalyst a coordination rhodium compound having the formula:

[(aryl)$_3$P]$_3$Rh$^+$(counterion)$^-$ or

[(aryl)$_3$P]$_3$Rh(CO)$_n$$^+$(counterion)$^-$ wherein aryl is phenyl, phenyl substituted by 1 to 3 methyl groups, or for one aryl group, polystyryl, n is the integer 1 or 2, (counterion)$^-$ is the conjugate base of acids selected from HC(R)(SO$_2$R$_f$)$_2$, R$_f'$SO$_3$H, and HN(SO$_2$R$_f$)$_2$ wherein R$_f$ is a perfluoroalkyl group having 1 to 20 carbon atoms, R$_f'$ is a perfluoroalkyl group having 4 to 20 carbon atoms, and R is lower alkyl, phenyl, Cl, H, SO$_2$R$_f$, or R$_f$.

10. The process according to claim 9 wherein the (counterion)$^-$ of said coordination compound is HC(SO$_2$CF$_3$)$_2$$^-$, HC(SO$_2$C$_4$F$_9$)$_2$$^-$, HC(SO$_2$C$_8$F$_{17}$)$_2$$^-$, C$_6$H$_5$C(SO$_2$CF$_3$)$_2$$^-$, N(SO$_2$CF$_3$)$_2$$^-$, C$_8$F$_{17}$SO$_3$$^-$, or C$_8$F$_{15}$SO$_3$$^-$.

11. The process according to claim 9 wherein R is the (counterion)$^-$ of said coordination compound is lower alkyl, phenyl, or hydrogen.

12. The process according to claim 9 wherein said coordination compound is selected from the class consisting of:

[(C$_6$H$_5$)$_3$P]$_3$Rh$^+$HC(SO$_2$CF$_3$)$_2$$^-$,

[(C$_6$H$_5$)$_3$P]$_3$RH$^+$C$_6$H$_5$C(SO$_2$CF$_3$)$_2$$^-$,

[(C$_6$H$_5$)$_3$P]$_3$Rh$^+$N(SO$_2$CF$_3$)$_2$$^-$,

[(C$_6$H$_5$)$_3$P]$_3$Rh$^+$HC(SO$_2$C$_8$F$_{17}$)$_2$$^-$,

[(C$_6$H$_5$)$_3$P]Rh$^+$HC(SO$_2$C$_4$F$_9$)$_2$$^-$,

[(p-tolyl)$_3$P]$_3$Rh$^+$HC(SO$_2$C$_4$F$_9$)$_2$$^-$,

[(C$_6$H$_5$)$_3$Rh(CO)$_2$$^+$HC(SO$_2$CF$_3$)$_2$$^-$,

[(C$_6$H$_5$)$_3$P]$_3$Rh(CO)$^+$HC(SO$_2$CF$_3$)$_2$$^-$,

[(C$_6$H$_5$)$_3$P]$_3$Rh$^+$C$_8$F$_{17}$SO$_3$$^-$, and

[(C$_6$H$_5$)$_3$P]$_3$Rh$^+$C$_8$F$_{15}$SO$_3$$^-$.

* * * * *